United States Patent [19]

Lisnyansky et al.

[11] Patent Number: 4,963,229

[45] Date of Patent: Oct. 16, 1990

[54] SYSTEM AND METHOD FOR CONTINUOUS MEASUREMENT OF PULP CONSISTENCY IN A BLOWLINE OF A CONTINUOUS PULP DIGESTER

[75] Inventors: Khaim Lisnyansky; H. Heinz Walbaum, both of Chester, N.Y.

[73] Assignee: International Paper Company, Purchase, N.Y.

[21] Appl. No.: 751,365

[22] Filed: Jul. 2, 1985

[51] Int. Cl.$^5$ ............................ D21C 7/12; D21F 7/06
[52] U.S. Cl. ...................................... 162/49; 162/238; 162/263; 162/DIG. 10; 73/61 R; 73/61.1 R
[58] Field of Search .................... 162/49, 238, 60, 252, 162/263, 61, 17, 19, DIG. 10; 73/61 R, 61.1 R; 137/4, 88

[56] References Cited

U.S. PATENT DOCUMENTS

| | | | |
|---|---|---|---|
| 3,322,616 | 5/1967 | Hutchinson et al. | 162/238 |
| 3,764,463 | 10/1973 | Histed et al. | 162/49 |
| 3,802,964 | 4/1974 | Forgacs et al. | 162/263 |
| 3,822,179 | 7/1974 | Chari et al. | 162/17 |
| 3,994,602 | 11/1976 | Howarth | 356/208 |
| 4,012,197 | 3/1977 | Howarth | 162/49 |
| 4,096,028 | 6/1978 | Rosenberger | 162/49 |
| 4,138,313 | 2/1979 | Hillstrum et al. | 162/49 |
| 4,141,784 | 2/1979 | Lofkrantz et al. | 162/49 |
| 4,146,422 | 3/1979 | Prough | 162/49 |
| 4,162,933 | 7/1979 | Sherman et al. | 162/49 |
| 4,239,590 | 12/1980 | Prough | 162/49 |
| 4,276,119 | 6/1981 | Karnis et al. | 162/49 |

FOREIGN PATENT DOCUMENTS

1002361 12/1976 Canada .
1035620 1/1978 Canada .

OTHER PUBLICATIONS

Granberg et al., *EUCEPA Symposium on Control Systems in Pulp and Paper*, "Kappa Number Control of Kamyr Digesters", May 11-14, 1982, Stockholm, Sweden.

Grace, et al., *Tappi*, "Effect of Composition on the Measurement of Black Liquor Solids Content by a Refractometer and a Sonic Velocimeter", vol. 58, No. 5, May, 1975, pp. 117-120.

Chamberlain et al., *Computer Control*, "Control Your Recovery Furnace Distrubances", vol. 75, No. 12, Dec., 1974, pp. 79-84.

Morgan, Paper and Pulp Canada, "How We Wash Brown Stock at Crestbrook", vol. 7, No. 2, Feb., 1975, pp. 57-61.

*Primary Examiner*—Steve Alvo
*Attorney, Agent, or Firm*—Charles B. Smith; Wayne M. Kennard

[57] ABSTRACT

A system and method to continuously determine the pulp consistency in the discharge blowline (112) of a continuous pulp digester (100) having a gamma gauge (116) disposed adjacent to the blowline (112) for continuous measurement of the intensity of gamma radiation attenuated by the pulp slurry passing through the blowline (112), a density gauge (118) disposed adjacent to a cold blow liquor line (102) for continuous measurement of the density of the cold blow liquor in the cold blow line (102) independent of variations in the gamma radiation mass-attenuation coefficient of the cold blow liquor in the cold blow liquor line (102), a gamma gauge (120) disposed adjacent to the cold blow liquor line (102) for measuring the intensity of gamma radiation attenuated by the cold blow liquor passing through the cold blow liquor line (102) and a computer (122) for receiving signals output from the first gamma gauge (116), the density gauge (118) and the second gamma gauge (120) indicative of intensity of gamma radiation attenuated by pulp slurry, the density of the cold blow liquor and the intensity of gamma radiation attenuated by the cold blow liquor respectively, and calculating the pulp consistency in the pulp slurry based on these received signals.

13 Claims, 1 Drawing Sheet

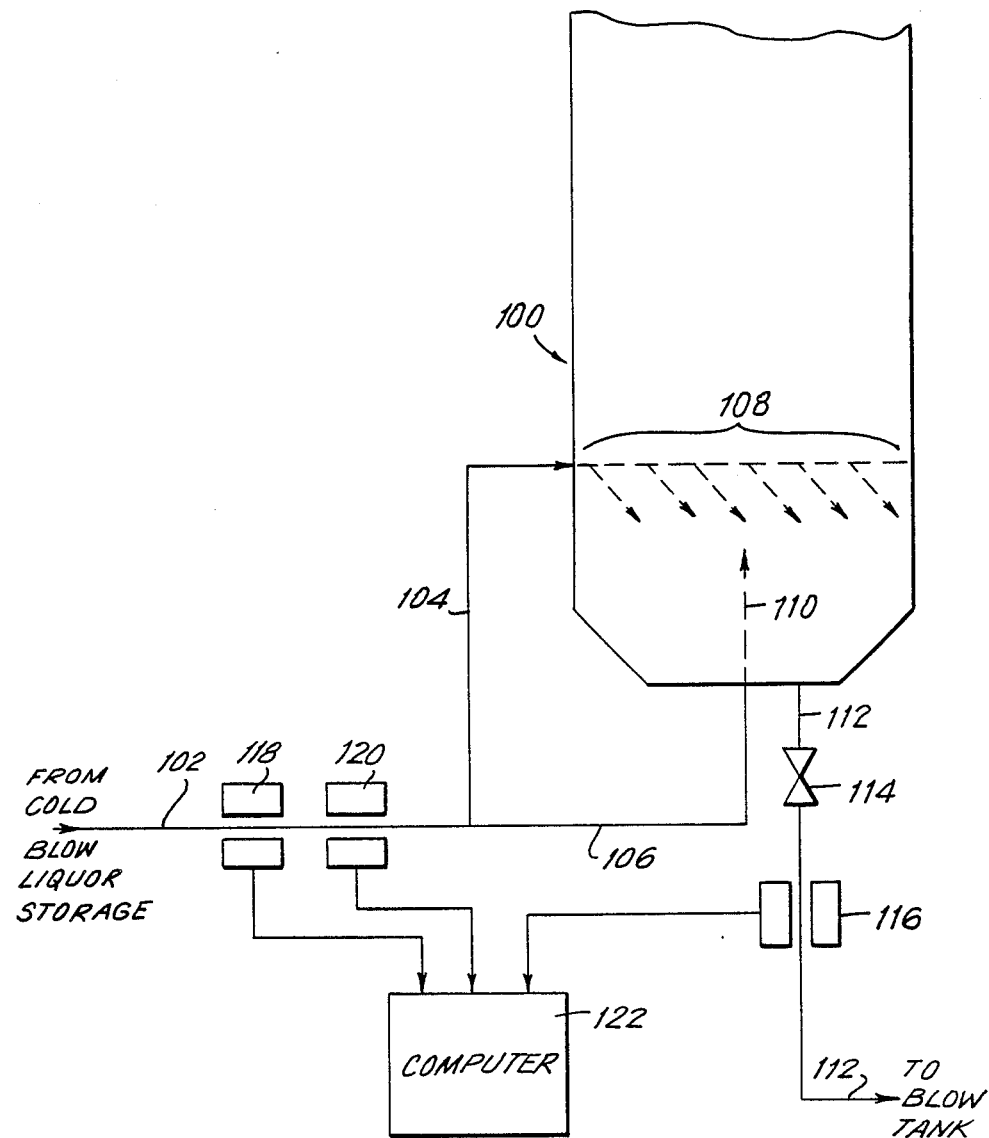

SYSTEM AND METHOD FOR CONTINUOUS MEASUREMENT OF PULP CONSISTENCY IN A BLOWLINE OF A CONTINUOUS PULP DIGESTER

TECHNICAL FIELD

The present invention relates to systems and methods for continuous measurement of pulp consistency in a discharge blowline of a continuous pulp digester. The present invention, more specifically, relates to systems and methods for continuous measurement of pulp consistency in a blowline of a continuous pulp digester which utilizes the correlation between the density of the pulp slurry passing through the discharge blowline of the digester and the pulp consistency of the pulp slurry in the discharge blowline.

BACKGROUND ART

Since the development of continuous pulp digesters for pulp production, there has been a need to accurately measure pulp consistency of the pulp slurry in the discharge blowline at the discharge of the digester. The pulp consistency in the pulp slurry at the discharge of the digester together with pulp flow rate are the key variables for retention time control of the pulping process which affects the uniformity of the pulp produced.

The retention time of the cellulose fibers in the digester has a significant effect on the degree of delignification of the wood chips from which the cellulose fibers are released to produce a pulp slurry in which a desired amount of lignin is dissolved. Therefore, assuming all other conditions of the digestion process are constant, the shorter the retention time in the digester, the larger the content of lignin remaining within the cellulose fibers in the pulp slurry. Conversely, the longer the retention time in the digester, the smaller the lignin content remaining within the cellulose fibers in the pulp slurry.

There is presently no method to directly track the retention time of a given amount of cellulose (wood chips) in the digester. Therefore, indirect methods are used to determine the retention time in the continuous digester via measurement of certain characteristics of the pulp slurry in the discharge blowline of the digester. For example, systems have been devised to attempt to estimate pulp consistency in the blowline by measuring the power consumption of an outlet device which pumps the pulp slurry into the blowline. Systems have also been devised for measuring the differential pressure along the discharge blowline of the digester to determine pulp consistency. However, these types of measurement systems are influenced by the Kappa number, which is a measure of the residual lignin remaining with the cellulose fibers, and by the production rate. Granberg et al., *Kappa Number Control of Kamyr Digesters,* EUCEPA Symposium on "Control Systems in Pulp and Paper Industry," May 11–14, 1982, Stockholm, Sweden. Although such systems have met with some success, their overall acceptance has been limited because of their dependence on the Kappa number.

Attempts have been made to determine pulp consistency in the blowline by the combined use of a refractometer and a gamma gauge. In these systems, the refractometer and gamma gauge are disposed adjacent to the blowline for making measurements of certain characteristics of the pulp slurry in the blowline. The refractometer attempts to measure the density of the liquid phase of the pulp slurry, while the gamma gauge attempts to measure the total density of the pulp slurry in the blowline. From these measurements pulp consistency in the blowline was determined. U.S. Pat. Nos. 4,146,422 and 4,239,590; and Canadian Patent Nos. 1,002,361 and 1,035,620. This type system worked in some paper mills but other paper mills had problems due to refractometer failure. Granberg et al., *Kappa Number Control of Kamyr Digesters,* EUCEPA Symposium on "Control Systems in Pulp and Paper Industry," May 11–14, 1982, Stockholm, Sweden.

Furthermore, there are other substantive problems associated with the use of a refractometer to make measurements of the density of the liquid phase of the pulp slurry. One is that deposits can accumulate on the optical window of the refractometer in contact with the pulp slurry thereby preventing any accurate measurement by this device. Another is that the refractive index of any liquid is function of the liquid density and liquid composition; and since the latter depends on the organic and inorganic content of the liquid phase of the pulp slurry, measurements made by a refractometer can be inaccurate because organics usually have higher refractive indices than inorganics, but their densities have the opposite relationship. So, the measurements made by the refractometer are dependent on the composition of liquid phase of the pulp slurry immediately adjacent to the optical window of the refractometer.

The present invention overcomes these problems and provides a system and method to more accurately and reliably determine pulp consistency.

DISCLOSURE OF INVENTION

The present invention is a system and method for determining pulp consistency in the discharge blowline of a continuous pulp digester. The system and method of the present invention are particularly useful for continuous pulp digesters which have an outlet referred to as a discharge blowline and cold blow liquor line for providing pulp washing liquid referred to as cold blow liquor. Such continuous pulp digesters are conventional and commercially available from Kamyr, Inc., Glen Falls, N.Y.

In the system of the invention, a gamma gauge is disposed adjacent to the discharge blowline. This gamma gauge is configured to measure the density of the pulp slurry in the blowline. This measurement is influenced by the density and $\mu$-variations of the liquid phase of the pulp slurry ($\mu$ is the gamma radiation mass attenuation coefficient of the liquid phase of the pulp slurry).

The cold blow liquor dilution line has two devices disposed adjacent to it. The first device is a density gauge which measures the density of the cold blow liquor in the cold blow liquor line. This measurement of density is independent of the $\mu$-variations in the cold blow liquor which makes up 85% to 95% of the liquid phase of the pulp slurry after the pulp is washed with cold blow liquor in the bottom of the digester to replace the strong black liquor resulting from the digestion process. The second device is a gamma gauge which is configured to measure the density of the cold blow liquor. This measurement of density is influenced by $\mu$-variation in the cold blow liquor.

The signals derived from the gamma gauge disposed adjacent to the blowline, and the gamma gauge and density, gauge disposed adjacent to the cold blow liquor line are output from these devices and input to a computer or microprocessor of the system of the invention for calculating the pulp consistency in the pulp slurry passing through the blowline. These measurement values are used in calculating the pulp consistency independent of the $\mu$-variations of the cold blow liquor which could influence the ultimate determination of pulp consistency as will be described.

The system of the invention in a second embodiment includes a gamma gauge disposed adjacent to the discharge blowline and a single density measuring device, such as a gamma gauge or density gauge, disposed adjacent to the cold blow line. In the second embodiment, the $\mu$-value of the liquid phase of the pulp slurry is assumed to be constant, therefore, only one measurement device is required adjacent to the cold blow liquor line.

The signals derived from the gamma gauge adjacent to the blowline, and the density gauge or gamma gauge disposed adjacent to the cold blow liquor line are output from these devices and input to the computer of the system for use in calculating the pulp consistency in the pulp slurry passing through the blowline. Although the second embodiment remains influenced by the $\mu$-variations of the cold blow liquor making up a substantial portion of the liquid phase of the pulp slurry after washing the pulp to replace the strong black liquor, it eliminates the uncertainty of the measurement of pulp consistency using a refractometer as used in the prior art.

An object of the invention is to provide a system and method to determine pulp consistency in the discharge blowline of a continuous pulp digester based on the measurement and relationship of the densities of the pulp slurry in the blowline and the density of the cold blow liquor.

Another object of the present invention is to provide a system and method to determine pulp consistency in the discharge blowline of a continuous pulp digester in which compensation is made for $\mu$-variations in the cold blow liquor.

A further object of the invention is to provide a system and method to determine the pulp consistency in the discharge blowline of a continuous pulp digester which neglects the $\mu$-variations of the cold blow liquor but is more accurate and reliable in determining pulp consistency in the blowline than prior art systems.

These and other objects of the invention will be described in greater detail in the remaining portions of the disclosure.

BRIEF DESCRIPTION OF THE DRAWING

The FIGURE shows a schematic diagram of a portion of a continuous pulp digester having the system of the invention incorporated therein.

BEST MODE FOR CARRYING OUT THE INVENTION

Referring to the FIGURE the preferred embodiment of the system of the invention will be described.

The embodiments of the system of the invention are useful for determining the pulp consistency in discharge blowline 112 of conventional continuous pulp digester 100 which is commercially available from Kamyr, Inc., Glen Falls, N.Y.

Continuous digester 100 operates in a conventional manner to delignify wood chips supplied to the top of the digester to produce pulp containing cellulose fiber which is discharged from the bottom of the digester.

In the operation of conventional continuous pulp digester 100, the first washing stage of the pulp is carried out in the bottom of the digester prior to discharge of the pulp slurry. In this first washing stage, cold blow liquor from line 102 is supplied to lines 104 and 106 for input to digestor 100. The cold blow liquor washes the pulp in such a manner that the black liquor (strong cooking liquor), is substantially replaced in the pulp slurry with cold blow liquor. To accomplish this, the cold blow liquor is supplied in a conventional manner via peripheral nozzles 108 and line 110 to the bottom of the digester. The washed pulp is discharged as a pulp slurry from digester 100 into discharge blowline 112. The pulp slurry output from the digester is controlled by valve 114.

The basis upon which the system of the invention determines pulp consistency is based on the relationship between the density of the cold blow liquor in cold blow liquor line 102 and the density of the liquid phase of the pulp slurry in blowline 112. This relationship allows for making measurements of the density of cold blow liquor in cold blow liquor line 102 to provide the values of the density and $\mu$-variations of the liquid phase of the pulp slurry.

In the preferred embodiment of the system of the invention, gamma gauge 116 is disposed adjacent to blowline 112 to measure the density of the pulp slurry in blowline 112. Gamma gauge 116, for example, is commercially available from Texas Nuclear, Inc., Austin, Tex. Cold blow liquor line 102 has density gauge 118 and gamma gauge 120 disposed adjacent to it. Density gauge 118 is a conventional density gauge such as Dynatrol Density Cell, commercially available from Automation Products, Inc., Houston, Tex. Density gauge 118 measures the density of the cold blow liquor in line 102. This measurement of density is independent of $\mu$-variations of the cold blow liquor. Gamma gauge 120 is the same type of gamma gauge as gamma gauge 116, and is commercially available from the same manufacturer. Gamma gauge 120 also measures the density of the cold blow liquor in cold blow liquor line 102 but this measurement is influenced by the $\mu$-variations of the cold blow liquor.

It has been found that by determining the density and $\mu$-value of the cold blow liquor, estimates can be made of these variables in the liquid phase of the pulp slurry since the displacement ratio of black liquor with cold blow liquor during the first washing step in the bottom of the digester is very high. This displacement of the liquid phase of the pulp slurry during the first washing step is highly efficient and yields a displacement ratio of between 85%-95%. Morgen, J. P., *How We Wash Brown Stock at Crestbrook*, Pulp and Paper, Canada, Vol. 76, No. 2, pp. 57-61. Because of the high efficiency of the washing of the pulp, the pulp slurry output from the digester into blowline 112 consists of cellulose fibers and blowline liquor, where the blowline liquor is 85%-95% cold blow liquor and 5%-15% residual black liquor. Therefore, the density and $\mu$-variations of the blowline liquor can be reliably determined by measurement of the density and $\mu$-variations of the cold blow liquor which makes up a substantial percentage of the blowline liquor.

The correlation between the densities of the cold blow liquor and pulp slurry liquor is strong. By regression analysis, it has been determined that the correlation between these two densities yields an $R^2$ of approximately 0.8. Since this correlation coefficient is high, given densities and $\mu$-values of the cold blow liquor can be used to determine the density and $\mu$-value of the blowline liquor to determine pulp consistency in the blowline. The relationship between pulp slurry liquor density and cold blow liquor density, as determined for a particular continuous digester can be expressed by the equation:

$$\rho_{L1} = 0.0223 + 0.9880(\rho_{L2}) \tag{1}$$

where, $\rho_{L1}$ = the density of the blowline liquor at 70° C., g/cm³.

$\rho_{L2}$ = the density of the cold blow liquor at 70° C., g/cm³.

The R² of the correlation expressed in equation (1) is 0.82. By using this correlation between these two densities and the ability to compensate for the $\mu$-variations of the blowline liquor, pulp consistency in the blowing can be calculated, as will be described subsequently.

The method of calculating pulp consistency will now be described for the preferred embodiment of the system of the invention. The attenuation of gamma radiation in pulp slurry can be expressed by equation:

$$I_{\gamma 1} = I_{\gamma 10} e^{-(\mu_F M_F + \mu_{L1} M_{L1})} \tag{2}$$

where, $I_{\gamma 1}$ = the intensity of the gamma radiation attenuated by the pulp slurry.

$I_{\gamma 10}$ = the intensity of the unattenuated gamma radiation.

$\mu_F$ = the gamma radiation mass-attenuation coefficient of the cellulose material in the pulp slurry.

$\mu_{L1}$ = the gamma radiation mass-attenuation coefficient of the liquid phase of the pulp slurry.

$M_F$ = the mass per unit area of cellulose material in the blowline.

$M_{L1}$ = the mass per unit area of liquor in the blowline.

The attenuation of gamma radiation by the cold blow liquor in cold blow liquor line 102 can be expressed by the equation:

$$I_{\gamma 2} = I_{\gamma 20} e^{-\mu_{L2} M_{L2}} \tag{3}$$

where, $\mu_{L2}$ = the gamma radiation mass-attenuation coefficient of liquor in cold blow liquor line 102.

$M_{L2}$ = the mass per unit area of liquor in cold blow liquor line 102.

The diameter of the blowline can be expressed by the equation:

$$d_1 = \frac{M_F}{\rho_F} + \frac{M_{L1}}{\rho_{L1}} \tag{4}$$

where, $\rho_F$ = the density of cellulose fiber in blowline 112.

$\rho_{L1}$ = the density of liquor in blowline 112.

The diameter of cold blow liquor line 102 can be expressed by the equation:

$$d_2 = \frac{M_{L2}}{\rho_{L2}} \tag{4a}$$

The correlation between the density of the liquor in the pulp slurry in blowline 112 and the density of the cold blow liquor in cold blow liquor line 102, as shown in equation (1), can be generally expressed by the equation:

$$\rho_{L1} = a + b\rho_{L2} \tag{5}$$

where, a = intercept coefficient of the regression analysis curve.

b = slope coefficient of the regression analysis curve.

The consistency of cellulose fiber in blowline 112 can be expressed by the equation:

$$C_F = \frac{M_F}{M_F + M_{L1}} \tag{6}$$

Assuming that $\mu_{L1} \cong \mu_{L2} = \mu_L$ because the liquid phase of the pulp slurry in blowline 112 is 85–95% cold blow liquor, solving equations (2), (3), (4), (4a) and (5) for $M_F$ and $M\rho_{L1}$ and substituting for these terms in equation (6), pulp consistency can be expressed by the equation:

$$C_F = \frac{1}{1 + \dfrac{(a + b\rho_{L2})\left(\dfrac{\gamma_1}{d_1 \rho_F} + \mu_F\right)}{\left(\dfrac{a}{\rho_{L2}} + b\right)\dfrac{\gamma_2}{d_2} - \dfrac{\gamma_1}{d_1}}} \tag{7}$$

where, $$\gamma_1 = \ln \frac{I_{\gamma 1}}{I_{\gamma 10}}$$

$$\gamma_2 = \ln \frac{I_{\gamma 2}}{I_{\gamma 20}}$$

In equation (7), the values of a, b, $d_1$, $d_2$, $\mu_F$, $\rho_F$, $I_{\gamma 10}$ and $I_{\gamma 20}$ are constants and programmed into computer 122. The variables $I_{\gamma 1}$, $I_{\gamma 2}$ and $\rho_{L2}$ are determined continuously by gamma gauge 116, density gauge 118 and gamma gauge 120, respectively, and are continuously input to computer 122. Computer 122, in accordance with equation (7), calculates the pulp consistency, $C_F$. Further, it is noted that equation (7) does not contain the $\mu_L$ term, therefore, the determination of pulp consistency $C_F$ is independent of $\mu_L$- variations.

Referring to the FIGURE, the second embodiment of the system of the invention will be described. In the second embodiment of the system of the invention, gamma gauge 116 is disposed adjacent to blowline 112 to determine the density of the pulp slurry in the blowline. However, cold blow liquor line 102 has disposed adjacent to it, either density gauge 118 or gamma gauge 120. In this embodiment, the $\mu$-variations of the liquid phase of the pulp slurry (which is 85%–95% cold blow liquor) will influence the calculated value for pulp consistency. Even though the determination of pulp consistency is influenced by $\mu$-variations of the liquid phase of the pulp, the calculated value of pulp consistency, $C_F$, is a more accurate measurement of pulp consistency than that of any prior art systems.

In the second embodiment, as stated, only two measurement devices are used, one to measure the density of the pulp slurry, gamma gauge 116, and one to measure the density of the cold blow liquor, either density gauge 118 or gamma gauge 120. The relationship of the constituents of the pulp slurry in blowline 112 is expressed by the equation:

$$\frac{1}{\rho_p} = \frac{C_F}{\rho_F} + \frac{C_L}{\rho_{L1}}, \quad (8)$$

where $\rho_p$ = the density of the pulp slurry in blowline 112.
$C_L$ = the blowline liquor concentration in blowline 112.

Taking into consideration that $C_F + C_L = 1$ and solving equation (8) for pulp consistency, the following equation is derived:

$$C_F = \frac{(\rho_p - \rho_{L1})\rho_F}{(\rho_F - \rho_{L1})\rho_p} \quad (9)$$

By substituting the $\rho_{L1}$ term from equation (5) into equation (9), the following equation is derived:

$$C_F = \frac{(\rho_p - a - b\rho_{L2})\rho_F}{(\rho_F - a - b\rho_{L2})\rho_p} \quad (10)$$

In equation (10), the values of a, b, and $\rho_F$ are constants and are programmed into computer 122. The values of $\rho_p$ and $\rho_{L2}$ are continuously measured by gamma gauge 116, and density gauge 118 or gamma gauge 120, respectively, and provided continuously to computer 122 to determine the value of pulp consistency in blowline 112.

The preferred method for the system of the invention is carried out by the simultaneous steps of continuously measuring the density of the pulp slurry in blowline 112, continuously monitoring the cold blow liquor in cold blow liquor line 102 with two devices, one of which is a gamma gauge.

Following the simultaneous measuring steps, signals generated by gamma gauge 116, density gauge 118 and gamma gauge 120 indicative of their respective density measurements are continuously input to the system computer. Subsequent the inputting steps, the computer continuously calculates the pulp consistency in blowline 112 according to the equation:

$$C_F = \frac{1}{1 + \dfrac{(a + b\rho_{L2})\left(\dfrac{\gamma_1}{d_1\rho_F} + \mu_F\right)}{\left(\dfrac{a}{\rho_{L2}} + b\right)\dfrac{\gamma_2}{d_2} - \dfrac{\gamma_1}{d_1}}} \quad (11)$$

The method of operation of the second embodiment of the invention is carried out by the simultaneous steps of continuously measuring the density of the pulp slurry in blowline 112, and continuously measuring the density of cold blow liquor in cold blowline 102. Following the simultaneous measuring steps and continuously inputting to the system computer the signals indicative of the densities measured during the simultaneous measuring step, the calculating step is carried out to continuously determine the pulp consistency in the blowline with the computer according to the equation:

$$C_F = \frac{(\rho_p - a - b\rho_{L2})\rho_F}{(\rho_F - a - b\rho_{L2})\rho_p} \quad (12)$$

The terms and expressions which are employed here are used as terms of description and not of limitation, and there is no intention, in the use of such terms and expressions, of excluding the equivalents of the features shown and described, or portions thereof, it being recognized that various modifications are possible within the scope of the invention as claimed.

We claim:

1. A system for continuously determining pulp consistency in a discharge blowline of a continuous pulp digester having a cold blow liquor line for providing cold blow liquor to the digester to wash the pulp by substantially replacing strong black liquor in the pulp slurry with cold blow liquor prior to discharging the pulp slurry into the discharge blowline of the digester comprising:

a first measurement means disposed adjacent to the blowline for continuous measurement of the intensity of attenuated gamma radiation by the pulp slurry passing through the blowline;

a second measurement means disposed adjacent to the cold blow liquor line for continuous measurement of the density of the cold blow liquor passing through the cold blow liquor line independent of variations in the gamma radiation mass-attenuation coefficient of the cold blow liquor and for continuous generation of signals indicative of the density of the cold blow liquor independent of variations in the gamma radiation mass-attenuation coefficient of the cold blow liquor;

a third measurement means disposed adjacent to the cold blow liquor line for continuous measurement of the intensity of attenuated gamma radiation by the cold blow liquor passing through the cold blow liquor line; and a computing means connected to the first, second and third measurement means for calculating pulp consistency in the pulp slurry passing through the blowline based on the continuous signals received from the first, second and third measurement means which are indicative of the attenuation of gamma radiation by the pulp slurry, cold blow liquor density independent of variations in the gamma radiation mass-attenuation coefficient of the cold blow liquor, and the attenuation of gamma radiation by the cold blow liquor, respectively.

2. The system as recited in claim 1, wherein the computing means continuously determines pulp consistency in the pulp slurry passing through the blowline according to the equation:

$$C_F = \frac{1}{1 + \dfrac{(a + b\rho_{L2})\left(\dfrac{\gamma_1}{d_1\rho_F} + \mu_F\right)}{\left(\dfrac{a}{\rho_{L2}} + b\right)\dfrac{\gamma_2}{d_2} - \dfrac{\gamma_1}{d_1}}}, \quad (7)$$

where $C_F$ = the pulp consistency in the blowline, a = the intercept of a regression analysis curve of a graph of pulp slurry liquor density vs. cold blow liquor density, b = the slope of a regression analysis curve of a graph of the density of the liquor in the pulp slurry vs. cold blow liquor density, $\rho_{L2}$ = the density of the cold blow liquor in the cold blow line measured by the second measurement means, $$\gamma_1 = \text{the } \ln \frac{I_{\gamma 1}}{I_{\gamma 10}}$$

in which $I_{\gamma 1}$ is the intensity of the gamma radiation attenuated by the pulp slurry of $I_{\gamma 10}$ is the intensity of unattenuated gamma radiation as measured by the first measurement means, $d_1$ = the diameter of the blowline,
$\rho_F$ = the density of cellulose fiber,
$\mu_F$ = the gamma radiation mass-attenuation coefficient of cellulose fiber,
$d_2$ = the diameter of the cold blow liquor line, $$\gamma_2 = \text{the } \ln \frac{I_{\gamma 2}}{I_{\gamma 20}}$$

in which $I_{\gamma 2}$ is the intensity of the gamma radiation attenuated by the cold blow liquor and $I_{\gamma 20}$ is the unattenuated gamma radiation as measured by the third measurement means.

3. The system as recited in claim 1, wherein the first and third measurement means are gamma gauges.

4. The system as recited in claim 1, wherein the second measurement means is a density gauge.

5. A system for continuously determining pulp consistency in a discharge blowline of a continuous pulp digester having a cold blow liquor line for providing cold blow liquor to the digester to wash the pulp by substantially replacing strong black liquor in the pulp slurry with cold blow liquor prior to discharging the pulp slurry into the discharge blowline of the digester comprising:
 a first measurement means disposed adjacent to the blowline for continuous measurement of the density of the pulp slurry passing through the blowline and for continuous generation of signals indicative of the pulp slurry density;
 a second measurement means disposed adjacent to the cold blow liquor line for continuous measurement of the density of the cold blow liquor passing through the cold blow liquor line to predict the density of pulp slurry liquor in the discharge blowline and for continuous generation of signals indicative of the density of the cold blow liquor; and
 a computing means connected to the first and second measurement means for calculating pulp consistency in the pulp slurry passing through the blowline based on the continuous signals received from the first and second measurement means which are indicative of pulp slurry density and cold blow liquor density, respectively.

6. The system as recited in claim 5, wherein the computing means continuously determines pulp consistency in the pulp slurry passing through the blowline according to the equation:

$$C_F = \frac{(\rho_p - a - b\rho_{L2})\rho_F}{(\rho_F - a - b\rho_{L2})\rho_p},$$

where
$C_F$ = the pulp consistency in the blowline, $\rho_p$ = the density of the pulp slurry in the blowline as measured by the first measurement means,
$a$ = the intercept of a regression analysis curve of a graph of pulp slurry liquor density vs. cold blow liquor density,
$b$ = the slope of a regression analysis curve of a graph of pulp slurry liquor density vs. cold blow liquor density,
$\rho_{L2}$ = density of cold blow liquor in the cold blow liquor line as measured by the second measurement means,
$\rho_F$ = the density of cellulose fiber.

7. The system as recited in claim 5, wherein the first measurement means includes a gamma gauge.

8. The system as recited in claim 5, wherein the second measurement means includes a gamma gauge.

9. The system as recited in claim 5, wherein the second measurement means includes a density gauge.

10. A method of continuously determining pulp consistency in a discharge blowline of a continuous pulp digester having a cold blow liquor line for providing cold blow liquor to the digester for washing the pulp by substantially replacing strong black liquor in the pulp slurry with cold blow liquor prior to discharging the pulp slurry into the discharge blow line of the digester comprising the steps of:
 continuously measuring the intensity of the attenuated gamma radiation by the pulp slurry in the blowline and continuously generating signals indicative of the intensity of the attenuated gamma radiation by the pulp slurry in the blowline,
 continuously measuring the density of the cold blow liquor passing through the cold blow liquor line independent of variations in the gamma radiation mass-attenuation coefficient of the cold blow liquor and continuously generating signals indicative of the density of the cold blow liquor independent of variations in the gamma radiation mass-attenuation coefficient of the cold blow liquor;
 continuously measuring the intensity of the attenuated gamma radiation by the cold blow liquor passing through the cold blow liquor line and continuously generating signals indicative of the density of the cold blow liquor; and
 continuously computing the pulp consistency of the pulp slurry passing through the blowline with a computer based on continuous signals received by the computer indicative of the intensity of attenuated gamma radiation by the pulp slurry, the density of the cold blow liquor uninfluenced by variations in the gamma radiation mass-attenuation coefficient of the cold blow liquor and the intensity of attenuated gamma radiation by the cold blow liquor.

11. The method as recited in claim 10, wherein during the computing step pulp consistency is computed by the computer according to the equation:

$$C_F = \frac{1}{1 + \frac{(a + b\rho_{L2})\left(\frac{\gamma_1}{d_1\rho_F} + \mu_F\right)}{\left(\frac{a}{\rho_{L2}} + b\right)\frac{\gamma_2}{d_2} - \frac{\gamma_1}{d_1}}},$$

where
$C_F$ = pulp consistency in the blowline, a = the intercept of a regression analysis curve of a graph of pulp slurry liquor density vs. cold blow liquor density, b = the slope of a regression analysis curve of a graph of pulp slurry liquor density vs. cold blow liquor density, $\rho_{L2}$ = density of the cold blow liquor independent variations in the gamma radiation mass-attenuation coefficient, $$\gamma_1 = \text{the } \ln \frac{I_{\gamma 1}}{I_{\gamma 10}}$$

in which $I_{\gamma 1}$ is the intensity of the gamma radiation attenuated by the pulp slurry and $I_{\gamma 10}$ is the intensity of unattenuated gamma radiation, $d_1$ = the diameter of the blowline,
$\rho_F$ = the density of cellulose fiber,
$d_2$ = the diameter of the cold blow liquor line, $$\gamma_2 = \text{the } \ln \frac{I_{\gamma 2}}{I_{\gamma 20}},$$

in which $I_{\gamma 2}$ is the

12. A method of continuously determining pulp consistency in a discharge blowline of a continuous pulp digester having a cold blow liquor line for providing cold blow liquor to the digester for washing the pulp by substantially replacing strong black liquor in the pulp slurry with cold blow liquor prior to discharging the pulp slurry into the discharge blowline of the digester comprising the steps of:

continuously measuring the density of the pulp slurry passing through the blowline and continuously generating signals indicative of the intensity of the pulp slurry;

continuously measuring the density of the cold blow liquor passing through the cold blow liquor line to predict the density of pulp slurry liquor in the discharge blowline and continuously generating signals indicative of the density of the cold blow liquor; and continuously computing the pulp consistency of the pulp slurry passing through the blowline with computing means based on continuous signals received by the computing means indicative of the density of the pulp slurry and the density of the cold blow liquor.

13. The method as recited in claim 12, wherein during the computing step pulp consistency is computed by the computer according to the equation:

$$C_F = \frac{(\rho_p - a - b\rho_{L2})\rho_F}{(\rho_F - a - b\rho_{L2})\rho_p},$$

where
$C_F$ = pulp consistency in the blowline,
$\rho_p$ = the density of the pulp slurry in the blowline,
a = the intercept of a regression analysis curve of a graph of pulp slurry liquor density vs. cold blow liquor density,
b = the slope of a regression analysis curve of a graph of pulp slurry liquor density vs. cold blow liquor density,
$\rho_{L2}$ = density of cold blow liquor in the cold blow line,
$\rho_F$ = the density of cellulose fiber.

* * * * *